US011491089B2

(12) United States Patent
Brahms et al.

(10) Patent No.: US 11,491,089 B2
(45) Date of Patent: Nov. 8, 2022

(54) RELOADABLE MICROCAPSULES

(71) Applicant: International Flavors & Fragrances Inc., New York, NY (US)

(72) Inventors: John Brahms, Morris Plains, NJ (US); Yabin Lei, Holmdel, NJ (US); Julie Wieland, Edison, NJ (US); Li Xu, Edison, NJ (US); Lewis Michael Popplewell, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 748 days.

(21) Appl. No.: 16/098,254

(22) PCT Filed: May 3, 2017

(86) PCT No.: PCT/US2017/030729
§ 371 (c)(1),
(2) Date: Nov. 1, 2018

(87) PCT Pub. No.: WO2017/192648
PCT Pub. Date: Nov. 9, 2017

(65) Prior Publication Data
US 2019/0159979 A1 May 30, 2019

Related U.S. Application Data

(60) Provisional application No. 62/331,230, filed on May 3, 2016.

(51) Int. Cl.
| | |
|---|---|
| *A61K 8/11* | (2006.01) |
| *A61Q 13/00* | (2006.01) |
| *A61K 8/04* | (2006.01) |
| *D06M 23/12* | (2006.01) |
| *A61K 8/37* | (2006.01) |
| *C11D 7/50* | (2006.01) |
| *C11D 3/43* | (2006.01) |
| *B01J 13/20* | (2006.01) |
| *A61K 8/87* | (2006.01) |
| *D06M 23/06* | (2006.01) |
| *A61K 9/06* | (2006.01) |
| *D06M 13/00* | (2006.01) |
| *A61K 9/50* | (2006.01) |
| *A61K 9/00* | (2006.01) |
| *A01N 25/28* | (2006.01) |
| *A01N 37/18* | (2006.01) |
| *A61K 8/25* | (2006.01) |
| *A61K 8/43* | (2006.01) |
| *A61K 8/65* | (2006.01) |
| *A61K 8/84* | (2006.01) |
| *A61Q 15/00* | (2006.01) |
| *A61Q 19/00* | (2006.01) |
| *C11D 3/00* | (2006.01) |

| | |
|---|---|
| *C11D 3/50* | (2006.01) |
| *C11D 11/00* | (2006.01) |

(Continued)

(52) U.S. Cl.
CPC ............... *A61K 8/11* (2013.01); *A01N 25/28* (2013.01); *A01N 37/18* (2013.01); *A61K 8/046* (2013.01); *A61K 8/25* (2013.01); *A61K 8/37* (2013.01); *A61K 8/375* (2013.01); *A61K 8/43* (2013.01); *A61K 8/65* (2013.01); *A61K 8/84* (2013.01); *A61K 8/87* (2013.01); *A61K 9/0014* (2013.01); *A61K 9/06* (2013.01); *A61K 9/4808* (2013.01); *A61K 9/4816* (2013.01); *A61K 9/5005* (2013.01); *A61K 9/5031* (2013.01); *A61Q 13/00* (2013.01); *A61Q 15/00* (2013.01); *A61Q 19/00* (2013.01); *B01J 13/203* (2013.01); *C11D 3/0015* (2013.01); *C11D 3/43* (2013.01); *C11D 3/505* (2013.01); *C11D 7/5022* (2013.01); *C11D 11/0017* (2013.01); *C11D 17/0013* (2013.01); *C11D 17/0039* (2013.01); *D06M 13/005* (2013.01); *D06M 23/06* (2013.01); *D06M 23/12* (2013.01); *A61K 2800/412* (2013.01); *D06M 2200/50* (2013.01)

(58) Field of Classification Search
None
See application file for complete search history.

(56) References Cited

U.S. PATENT DOCUMENTS

| | | |
|---|---|---|
| 5,292,533 A | 3/1994 | McMahon et al. |
| 5,466,460 A | 11/1995 | McMahon et al. |

(Continued)

FOREIGN PATENT DOCUMENTS

| | | |
|---|---|---|
| EP | 2298439 A2 | 3/2011 |
| EP | 2963103 A1 * | 1/2016 |

(Continued)

OTHER PUBLICATIONS

"Euclidean Distance", Sep. 2005 (accessed from http://www.pbarrett.net/techpapers/euclid.pdf).*

(Continued)

*Primary Examiner* — Robert A Wax
*Assistant Examiner* — Randeep Singh
(74) *Attorney, Agent, or Firm* — Licata & Tyrrell P.C.

(57) ABSTRACT

A reloadable microcapsule contains a microcapsule core and a microcapsule wall encapsulating the microcapsule core. The microcapsule core contains a hydrophobic core solvent and a hydrophilic core solvent, and the microcapsule wall, formed of an encapsulating polymer, is permeable to the hydrophilic core solvent. Also disclosed are methods of preparing the reloadable microcapsule and consumer products having the microcapsules.

10 Claims, No Drawings

(51) Int. Cl.
*C11D 17/00* (2006.01)
*A61K 9/48* (2006.01)

(56) References Cited

U.S. PATENT DOCUMENTS

| | | | |
|---|---|---|---|
| 6,045,835 | A | 4/2000 | Soper et al. |
| 6,599,627 | B2 | 7/2003 | Yeo et al. |
| 7,108,860 | B2 | 9/2006 | Dueva et al. |
| 7,491,687 | B2 | 2/2009 | Popplewell et al. |
| 8,648,028 | B2 | 2/2014 | Looft |
| 8,722,026 | B2 | 5/2014 | Niki et al. |
| 9,119,973 | B2 | 9/2015 | Warr et al. |
| 9,464,263 | B2 | 10/2016 | Aussant et al. |
| 2002/0160109 | A1* | 10/2002 | Yeo .......... A61P 5/00 427/213.3 |
| 2005/0112152 | A1 | 5/2005 | Popplewell et al. |
| 2005/0153135 | A1* | 7/2005 | Popplewell et al. |
| 2005/0227907 | A1 | 10/2005 | Lee et al. |
| 2007/0042182 | A1 | 2/2007 | Markus et al. |
| 2009/0280079 | A1 | 11/2009 | Gray et al. |
| 2010/0086575 | A1 | 4/2010 | Dihora et al. |
| 2011/0077375 | A1 | 3/2011 | Kulke et al. |
| 2013/0295149 | A1 | 11/2013 | Ouali et al. |
| 2014/0017287 | A1 | 1/2014 | Lei et al. |
| 2014/0227328 | A1 | 8/2014 | Dihora et al. |
| 2014/0287008 | A1 | 9/2014 | Lei et al. |
| 2015/0017214 | A1 | 1/2015 | Warr et al. |

FOREIGN PATENT DOCUMENTS

| | | | |
|---|---|---|---|
| WO | 2013000587 | A1 | 1/2013 |
| WO | 2013092958 | A1 | 6/2013 |
| WO | WO2014011860 | * | 1/2014 |
| WO | 2015023961 | A1 | 2/2015 |
| WO | 2016049456 | A1 | 3/2016 |
| WO | 2016054351 | A1 | 4/2016 |

OTHER PUBLICATIONS

Extended European Search Report dated Dec. 19, 2019 for EP 17793205.0, filed May 3, 2017.
Ghose et al. (1998) "Prediction of Hydrophobic (Lipophilic) Properties of Small Organic Molecules Using Fragmental Methods: An Analysis of ALOGP and CLOGP Methods," J. Phys. Chem. A 102(21):3762-72.
Hongmao (2016) In: A Practical Guide to Rational Drug Design, Chapter 6, "Quantitative Structure-Property Relationships Models for Lipophilicity and Aqueous Solubility," pp. 193-223.
International Preliminary Report on Patentability in PCT/US2017/030729 dated Nov. 6, 2018.
International Search Report and Written Opinion in PCT/US2017/030729 dated Aug. 16, 2017.
Mannhold et al. (2009) "Calculation of Molecular Lipophilicity: State-of-the-Art and Comparison of LogP Methods on More than 96,000 Compounds," Journal of Pharmaceutical Sciences 98(3):861-893.
Office Communication dated Dec. 14, 2018 from U.S. Appl. No. 15/808,845, filed Nov. 9, 2017.
Office Communication dated Aug. 19, 2019 from U.S. Appl. No. 15/808,845, filed Nov. 9, 2017.
Office Communication dated Jul. 22, 2020 from U.S. Appl. No. 15/808,845, filed Nov. 9, 2017.
Office Communication dated Jan. 27, 2021 from U.S. Appl. No. 15/808,845, filed Nov. 9, 2017.
Pyka et al. (2006) "A Comparison of Theoretical Methods of Calculation of Partition Coefficients for Selected Drug," Acta Pol. Pharm. 63(3):159-67.

\* cited by examiner

RELOADABLE MICROCAPSULES

CROSS REFERENCE TO RELATED APPLICATIONS

This application is a national stage entry under 35 USC 371 for International Application No. PCT/US2017/030729 filed May 03, 2017, which claims the benefit of priority from U.S. Applications Ser. No. 62/331,230, filed on May 3, 2016. The contents of both applications are incorporated by reference in their entirety.

BACKGROUND

Microcapsules are useful in a variety of applications where there is a need to deliver, apply, or release a fragrance or other active material in a time-delayed and controlled manner.

Conventional microcapsules each have a polymeric shell encapsulating an active material in a microcapsule core. The polymeric shell is typically formed via an interfacial polymerization reaction, namely, a polymerization that occurs at an interface between an aqueous phase and an oil phase. These microcapsules have been developed to provide good performance in various consumer products such as laundry detergents. See, e.g., U.S. Pat. Nos. 7,491,687, 6,045,835, US 2014/0287008, and WO 2015/023961. Polyurea microcapsules have been developed for delivering fragrances. Their preparation involves the polymerization reaction between wall-forming materials, e.g., a polyisocyanate and a polyamine. During the polymerization reaction, the polyisocyanate can react with many fragrance ingredients such as primary alcohols contained in a fragrance accord. The other wall-forming material polyamine is also reactive towards aldehyde fragrance ingredients. Primary alcohols and aldehydes are common ingredients in many fragrance accords. Such fragrances are not suitable to be encapsulated by conventional microcapsules. In addition, fragrance ingredients having a high water solubility are also unsuitable for conventional encapsulation as these ingredients tend to stay in the aqueous phase instead of being encapsulated in the microcapsule oil core. Challenges remain in encapsulating fragrances and other active materials without losing reactive or water-soluble ingredients.

There is a need to develop a microcapsule suitable for encapsulating fragrances having ingredients that either have a high water solubility or are reactive towards wall-forming materials.

SUMMARY

This invention is based on the discovery that reloadable microcapsules can be prepared in absence of an active material (e.g., fragrance), thus avoiding the reaction between the active material and a wall-forming material. This reloadable microcapsule unexpectedly improves substantivity of a free fragrance on fabric or skin. It provides a facile method for delivering active materials in consumer products.

Accordingly, one aspect of this invention relates to microcapsules each having a microcapsule core and a microcapsule wall. The microcapsule core is encapsulated in the microcapsule wall and contains a hydrophilic core solvent and/or a hydrophobic core solvent. The microcapsule wall, formed of an encapsulating polymer, is permeable to the hydrophilic core solvent and the active material.

In some embodiments, the microcapsule core, free of an active material (e.g., a fragrance), consists of a hydrophobic core solvent and a hydrophilic core solvent; the hydrophilic core solvent has a water solubility of 1 to 100 g/L, a weighted Hansen solubility parameter of 18 or greater, a Hansen polarizability of 4 or greater, and a Hansen h-bonding value of 5 or greater; and the hydrophobic core solvent has a weighted Hansen solubility parameter of 18 or less, a Hansen polarizability of 4 or less, and a Hansen h-bonding value of 5 or less. The weight ratio between the hydrophobic core solvent and the hydrophilic core solvent can be in the range of 1:9 to 9:1.

Examples of the hydrophilic core solvent include, but are not limited to, triethyl citrate, triacetin, benzyl acetate, ethyl acetate, propylene glycol, dipropylene glycol, glycol ethers, and combinations thereof. Exemplary hydrophobic core solvents are isopropyl myristate, $C_5$-$C_{50}$ (e.g., $C_5$-$C_{20}$ and $C_6$-$C_{15}$) tryglyceride (e.g., caprylic triglyceride, capric triglyceride, and a mixture thereof), D-limonene, silicone oil, mineral oil, and combinations thereof.

In other embodiments, the microcapsule has a size of 0.1 to 1000 μm in diameter. The weight ratio between the microcapsule core and the microcapsule wall is preferably in the range of 1:99 to 99:1 (e.g., 1:1 to 50:1, 5:1 to 50:1, and 5:1 to 20:1). Suitable encapsulating polymers for the microcapsule wall include polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), and combinations thereof.

Another aspect of this invention relates to microcapsule compositions each comprising any of the microcapsules described above and a continuous phase that has an external hydrophilic solvent and an active material, in which the microcapsule wall is permeable to the active material, the ratio between the microcapsule core and the active material is 1:99 to 99:1, and the active material is selected from the group consisting of a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, taste modulator, and combinations thereof.

Nonlimiting exemplary external hydrophilic solvents are water, ethanol, propanol, dipropylene glycol, propylene glycol, glycerin, diethyl phthalate, and combinations thereof.

In some microcapsule compositions, the active material is a fragrance having a weighted Hansen solubility parameter of 15 to 20, a Hansen polarizability of 5 or less, and a Hansen h-bonding value of 10 or less. In other microcapsule compositions, the fragrance contains two or more fragrance ingredients, 50 weight % or more of the fragrance ingredients have a water solubility of 0.1 g/L or less, 50 weight % or less of the fragrance ingredients have a vapor concentration of 100 μg/L or less, and 30 weight % or less of the fragrance ingredients have a C Log P of 3 or less. In still other microcapsule compositions, the Euclidean difference in solubility parameter between the fragrance and the hydrophilic core solvent is less than the Euclidean difference between the fragrance and the hydrophobic core solvent. In yet other microcapsule compositions, the Euclidean difference in solubility parameter between the fragrance and the hydrophobic core solvent is less than 5.

Any of the microcapsule compositions described above can further contain a deposition aid such as polyquaternium- 4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, and any combination thereof.

Also within the scope of this invention is a method of preparing any one microcapsule compositions described above. The method includes the steps of: (a) providing a microcapsule that has a microcapsule core and a microcapsule wall encapsulating the microcapsule core, in which the microcapsule core contains a hydrophilic core solvent and/or a hydrophobic core solvent, and the microcapsule wall is formed of an encapsulating polymer and permeable to the hydrophilic core solvent; (b) providing a continuous phase that has an external hydrophilic solvent and an active material; (c) mixing the microcapsule and the continuous phase to obtain a microcapsule dispersion; and (d) aging the microcapsule dispersion to obtain the microcapsule composition.

Still within the scope of this invention are consumer products containing any one of the microcapsule compositions described above. The consumer product can be liquid or semisolid products such as a shampoo, a hair conditioner, a hair rinse, a hair refresher, a hair fixative or styling aid, a hair bleach, a hair dye or colorant, a soap, a body wash, a body mist, a body spray, a non-aerosol body spray containing a suspending technology, insect repellent, a cosmetic preparation, an all-purpose cleaner, a bathroom cleaner, a floor cleaner, a window cleaner, a bath tissue, a paper towel, a disposable wipe, a diaper rash cream or balm, a baby powder, a diaper, a bib, a baby wipe, an oral care product, a tooth paste, an oral rinse, an tooth whitener, a denture adhesive, a chewing gum, a breath freshener, an orally dissolvable strips, a chewable candy, a hard candy, a hand sanitizer, an anti-inflammatory balm, an anti-inflammatory ointment, an anti-inflammatory spray, a health care device, a dental floss, a toothbrush, a tampon, a feminine napkin, a personal care product, a sunscreen lotion, a sunscreen spray, a wax-based deodorant, a glycol type deodorant, a soap type deodorant, a facial lotion, a body lotion, a hand lotion, a body powder, a shave cream, a bath soak, an exfoliating scrub, a foot cream, a facial tissue, a cleansing wipe, a fabric care product, a fabric softener, a fabric refresher, an ironing water, a liquid laundry detergent, a powder detergent, a liquid dish detergent, an automatic dish detergent, a unit dose tablet or capsule, a scent booster, a drier sheet, a fine fragrance, a solid perfume, a powder foundation, a liquid foundation, an eye shadow, a lipstick or lip balm, an Eau De Toilette product, a deodorant, a rug deodorizer, a candle, a room deodorizer, a disinfectant, an anti-perspirant, an roll-on product, or an aerosol product. An exemplary consumer product is an aerosol product containing 0.01 to 50% of any one of the above-described microcapsule compositions.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "capsule" and "microcapsule" are used interchangeably.

The terms "g," "mg," and "µg" refer to "gram," "milligram," and "microgram," respectively. The terms "L" and "mL" refer to "liter" and "milliliter," respectively.

The term "Hansen solubility parameter" refers to a solubility parameter approach proposed by Charles Hansen used to predict polymer solubility and was developed around the basis that the total energy of vaporization of a liquid consists of several individual parts. To calculate the "weighted Hansen solubility parameter" one must combine the effects of (atomic) dispersion forces, (molecular) permanent dipole-permanent dipole forces, and (molecular) hydrogen bonding (electron exchange). The "weighted Hansen solubility parameter" is calculated as $(\delta D^2+\delta P^2+\delta H^2)^{0.5}$, wherein $\delta D$ is the Hansen dispersion value, $\delta P$ is the Hansen polarizability value, and $\delta H$ is the Hansen Hydrogen-bonding ("h-bonding") value. For a more detailed description of the parameters and values, see Charles Hansen, The Three Dimensional Solubility Parameter and Solvent Diffusion Coefficient, Danish Technical Press (Copenhagen, 1967).

Euclidean difference in solubility parameter between a fragrance and a solvent is calculated as $(4*(\delta D_{solvent}-\delta D_{fragrance})^2+(P_{solvent}-\delta P_{fragrance})^2+(\delta H_{solvent}-\delta H_{fragrance})^2)^{0.5}$, in which $\delta D_{solvent}$, $\delta P_{solvent}$, and $\delta H_{sovent}$ are the Hansen dispersion value, Hansen polarizability value, and Hansen h-bonding values of the solvent, respectively; and $\delta D_{fragrance}$, $\delta P_{fragrance}$, and $\delta H_{fragrance}$ are the Hansen dispersion value, Hansen polarizability value, and Hansen h-bonding values of the fragrance, respectively.

The details of one or more embodiments of the invention are set forth in the description below. Other features, objects, and advantages will be apparent from the description and the claims.

DETAILED DESCRIPTION

It has been found that reloadable microcapsules formulated with a hydrophilic solvent unexpectedly improved substantivity of an active material (e.g., fragrance) not initially encapsulated in the microcapsules.

These microcapsules each have (i) a microcapsule wall permeable to both the hydrophilic core solvent and the active material (e.g., a fragrance) and (ii) a microcapsule core containing the hydrophilic core solvent alone or in combination with a hydrophobic core solvent. In a preferred embodiment, the microcapsule core consists of a hydrophilic solvent and a hydrophobic solvent and is free of an active material.

The reloadable microcapsule is then formulated with an active material in an external hydrophilic solvent. The hydrophilic core solvent is believed to diffuse from the microcapsule core to the external hydrophilic solvent and create a void in the microcapsule core. The active material diffuses in an opposite direction, i.e., from the external hydrophilic solvent to the void in the microcapsule core, thus affording a microcapsule composition without the need to encapsulating the active material during the preparation of the reloadable microcapsule.

Such a microcapsule composition is shown to be an effective delivery system capable of delivering a fragrance with enhanced longevity in an alcohol based carrier. By preparing a reloadable microcapsule without a fragrance, the delivery system can later incorporate a fragrance of choice into the reloadable microcapsule for a specific application. Thus, significant economies of scale and enhancements of creative flexibility can be achieved.

The microcapsule composition can assist the delivery of fragrance components with low substantivity, thereby expanding the fragrance pallet. The term substantivity refers to the property of the encapsulated fragrance to be retained on a solid surface (such as skin, hair, laundry, furniture, and floor) for a prolonged period of time.

The microcapsule composition also allows for the delivery of fragrance components with functional groups such as aldehydes and primary alcohols, which would otherwise react with capsule wall materials. These functional groups are indeed common in fragrances as well as other active materials.

Further, the microcapsule composition also has applicability in applications such as skin care products where topical substantivity of a hydrophobic semi-volatile skin care active is needed. Some non-limiting examples include sunscreens, topical analgesics, antibacterial agents, and combinations thereof.

Also envisioned is the ability of the microcapsule composition to enhance substantivity and release of a semi-volatile active in other applications such as cosmetics, pesticides, insect repellents, herbicides, and pheromone baits for pest control.

The microcapsule composition delivery system also find its utility in a wide range of consumer applications, e.g., personal care products including shampoos, hair conditioners, hair rinses, hair refreshers; personal wash such as bar soaps, body wash, personal cleaners and sanitizers; fabric care such as fabric refreshers, softeners and dryer sheets, ironing water, industrial cleaners, liquid and powder detergent including unit dose capsules, rinse conditioners, and scent booster products; fine fragrances such as body mist and Eau De Toilette products; deodorants; roll-on products, and aerosol products. A specific consumer product is an alcohol deodorant spray product.

Not to be bound by any theory, it is believed that, when mixing a reloadable microcapsule with an active material in an external hydrophilic solvent, the hydrophilic core solvent diffuses from the core to the external hydrophilic solvent, making space for the active material to diffuse from the external hydrophilic solvent to the microcapsule core until the equilibrium is reached.

The microcapsule wall has pores or channels making the wall permeable to both the hydrophilic core solvent and the active material. Permeability also relates to the thickness of the wall, which can be controlled or manipulated by the weight ratio between the microcapsule core and the microcapsule wall forming materials. This weight ratio can be 100:1 to 1:1 (e.g., 50:1 to 5:1 and 40:1 to 8:1). By using a higher ratio (namely more microcapsule core than microcapsule wall-forming materials), the microcapsule wall becomes thinner and is more permeable.

The microcapsule wall is formed of an encapsulating polymer that can be polyurea, polyurethane, alginate, gelatin, urea formaldehyde, melamine formaldehyde, acrylate hydrogel, polylactide, chitosan, silica, or a combination thereof.

Turning to the microcapsule core, it contains a hydrophilic core solvent. The water solubility of this solvent can be 0.02 to 300 g/L, preferably 0.1 to 200 g/L, and more preferably 1 to 100 g/L. The hydrophilic core solvent typically has a weighted Hansen solubility parameter of 18 or greater, a Hansen polarizability (SP) of 4 or greater, and a Hansen h-bonding value ($\delta H$) of 5 or greater. Exemplary hydrophilic core solvents are triethyl citrate, triacetin, benzyl acetate, ethyl acetate, propylene glycol, dipropylene glycol, and combinations thereof. More examples include glycol ethers such as ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether, diethylene glycol mono-n-butyl ether, ethylene glycol dimethyl ether, ethylene glycol diethyl ether, ethylene glycol dibutyl ether, and combinations thereof.

Besides the hydrophilic core solvent, the microcapsule core can also contain a hydrophobic core solvent having a weighted Hansen solubility parameter of 18 or less, a Hansen polarizability (SP) value of 4 or less, and a Hansen h-bonding value ($\delta H$) of 5 or less. These hydrophobic solvents, being nonvolatile (i.e., having a boiling point of 100° C. or higher), are added to modify the hydrophilicity/hydrophobicity of the microcapsule core solvents for optimized fragrance diffusion. In some embodiments, hydrophobic solvents are used to increase the compatibility of various active materials, increase the overall hydrophobicity of the core solvents, influence the vapor pressure, or serve to structure the mixture. Suitable solvents include those having reasonable affinity for the active materials and a C log P greater than 2.5, preferably greater than 3.5 and more preferably greater than 5.5. It should be noted that selecting a solvent and active material with high affinity for each other will result in improvement in stability. Exemplary solvents are triglyceride oil, mono and diglycerides, mineral oil, silicone oil, diethyl phthalate, polyalpha olefins, castor oil, isopropyl myristate, mono-, di- and tri-esters and mixtures thereof, fatty acids, and glycerine. The fatty acid chain can range from $C_4$-$C_{26}$ and can have any level of unsaturation. For instance, one of the following solvents can be used: capric/caprylic triglyceride known as NEOBEE M5 (Stepan Corporation); the CAPMUL series by Abitec Corporation (e.g., CAPMUL MCM); isopropyl myristate; fatty acid esters of polyglycerol oligomers, e.g., $R^2CO$—[$OCH_2$—CH($OCOR^1$)—$CH_2O$—]$_n$, where $R^1$ and $R^2$ can be H or $C_4$-$C_{26}$ aliphatic chains, or mixtures thereof, and n ranges between 2 and 50, preferably 2 and 30; nonionic fatty alcohol alkoxylates like the NEODOL surfactants by BASF; the dobanol surfactants by Shell Corporation or the BIO-SOFT surfactants by Stepan, wherein the alkoxy group is ethoxy, propoxy, butoxy, or mixtures thereof and said surfactants can be end-capped with methyl groups in order to increase their hydrophobicity; di- and tri-fatty acid chain containing nonionic, anionic and cationic surfactants, and mixtures thereof, fatty acid esters of polyethylene glycol, polypropylene glycol, and polybutylene glycol, or mixtures thereof, polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; di-octyl adipate and di-isodecyl adipate. In certain embodiments, ester oils have at least one ester group in the molecule. One type of common ester oil useful in the present invention are the fatty acid mono and polyesters such as cetyl octanoate, octyl isonanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER. Preferred examples are isopropyl myristate, $C_5$-$C_{50}$ tryglycerides (e.g., caprylic ($C_8$) triglyceride, capric ($C_{10}$) triglyceride, and a mixture thereof), D-limonene, silicone oil, and combinations thereof.

The ratio between the hydrophobic core solvent and the hydrophilic core solvent is 1:9 to 9:1 (e.g., 1:4 to 4:1 and 2:3 to 3:2). By way of illustration, the microcapsule core contains by weight a hydrophobic core solvent 10-90% (e.g., 20-80% and 40-60%) and a hydrophilic core solvent 10-90% (e.g., 20-80% and 40-60%), provided that the sum of the hydrophobic core solvent and the hydrophilic core solvent is 100% by weight of the microcapsule core.

When the reloadable microcapsule is dispersed in an external hydrophilic solvent, the hydrophilic core solvent diffuses to the external hydrophilic solvent as the affinity between the external hydrophilic solvent and the hydrophilic core solvent is greater than the affinity between the hydrophobic core solvent and the hydrophilic core solvent. The affinity is related to the Euclidean difference in solubility parameter described above. A small Euclidean difference indicates a strong affinity.

An active material (e.g., a fragrance) is present in the external hydrophilic solvent. In some embodiments, the active material has an affinity for the hydrophobic core solvent greater than that for either the hydrophilic core solvent or the external hydrophilic solvent, so that the active material is prone to diffuse into the microcapsule core. In other embodiments, the active material has a weighted Hansen solubility parameter of 20 or less (e.g., 15-20), a Hansen polarizability (SP) value of 5 or less, and a Hansen h-bonding value ($\delta H$) of 10 or less (e.g., 9 or less and 8 or less). In still other embodiments, the active material has a water solubility 0.2 g/L or less (e.g., 0.1 g/L or less) and/or a vapor concentration of 100 μg/L or more (i.e., the concentration of the vapor of the ingredient in the air to which it evaporates). When the active material is a fragrance containing multiple fragrance ingredients, 50 wt % or more (i.e., 50-100 wt %) of the fragrance ingredients has a water solubility of 0.1 g/L or less and/or 50 wt % or less (i.e., 0-50 wt %) of the fragrance ingredients has a vapor concentration of 100 μg/L or less.

The weight ratio between the hydrophilic core solvent and the hydrophobic core solvent can range from 1:99 to 99:1 (e.g., 10:90 to 90:10, 30:70 to 70:30, and 40:60 to 60:40).

The microcapsule wall is formed of an encapsulating polymer. Examples of the encapsulating polymer include polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), and combinations thereof.

A specific exemplary encapsulating polymer is polyurea, which is typically a product of the polymerization reaction of a polyisocyanate and a polyamine in the presence of a dispersant such as polyvinyl alcohol, condensed naphthalene sulfonate, and a combination thereof. Either aromatic polyisocyanates or aliphatic polyisocyanates can be used. Suitable aromatic polyisocyanates include those containing a phenyl, tolyl, xylyl, naphthyl, or diphenyl moiety, or a combination thereof. Examples are polyisocyanurates of toluene diisocyanate, trimethylol propane-adducts of toluene diisocyanate, methylene diphenyl diisocyanate, and trimethylol propane-adducts of xylylene diisocyanate. Suitable aliphatic polyisocyanates include a symmetric or asymmetric trimer of hexamethylene diisocyanate, a dimer of hexamethylene diisocyanate, a trimer of isophorone diisocyanate, a biuret of hexamethylene diisocyanate, and a combination thereof.

Suitable polyamines include hexamethylene diamine ("HMDA"), hexaethylenediamine, ethylenediamine, 1,3-diaminopropane, 1,4-diamino-butane, diethylenetriamine, pentaethylenehexamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, and a combination thereof.

The weight ratio between the polyisocyanate and the polyamine (e.g., HMDA) can be in the range of 99:1 to 1:99 (e.g., 50:1 to 1:50 and 20:1 to 20:1).

More microcapsule wall materials are described below and can also be found in publications such as U.S. Pat. No. 7,196,049, US 2014/0044760, WO 2014/011860, WO 2014/059087, WO 2016/049456, WO 2015/023961, and WO 2014/085287.

The reloadable microcapsule thus prepare typically has a particle size in the range of from 0.1 to 1000 microns (i.e., μm) in diameter (e.g., 0.5 to 500 microns, 1 to 200 microns, 2 to 50 microns, 5 to 25 microns, and 1 to 10 microns). The capsule size distribution can be narrow, broad, or multimodal.

1. Microcapsule Delivery Systems

Reloadable microcapsules can be prepared following encapsulation procedures known in the art, except that the active material is not encapsulated in the procedures. See for example U.S. Pat. Nos. 5,112,688, 6,329,057, and 6,261,483. Wall forming materials (i.e., encapsulating polymers) include a melamine formaldehyde, polyurethane, polysiloxanes, polyurea, polyamide, polyimide, polyvinyl alcohol, polyanhydride, polyolefin, polysulfone, polysaccharide, protein, polypeptide, polylactide (PLA), polyglycolide (PGA), polyorthoester, polyphosphazene, silicone, lipid, modified cellulose, gum, polystyrene, polyester, polyether, and combination of these materials. Other polymeric materials that are functional are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, and starch can also be used as the encapsulating materials. Additionally, capsules can be made via the simple or complex coacervation of gelatin. Preferred encapsulating wall polymers include those formed from isocyanates, acrylates, acrylamide, acrylate-co-acrylamide, hydrogel monomers, sol-gel precursors, gelatin, melamine-formaldehyde or urea-formaldehyde condensates, as well as similar types of aminoplasts.

Certain specific encapsulating polymers are described below as non-limiting examples.

1.1 Polyurea/Polyurethane Capsules

Polyurea capsules each have a microcapsule wall formed of an encapsulating polymer that is the polymerization reaction product of a polyisocyanate and a polyamine/polyalcohol. See WO 2004/054362; WO 2015/023961; and U.S. Pat. Nos. 6,340,653 and 8,299,011. In addition, the encapsulating polymer can also be prepared using a carbonyl crosslinker and a polyamine/polyalcohol.

1.1.1 Polyisocyanates

The polyisocyanates each contain two or more isocyanate (—NCO) groups. Suitable polyisocyanates include, for example, 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

Other suitable commercially-available polyisocyanates include LUPRANATE M20 (PMDI, commercially available from BASF containing isocyanate group "NCO" 31.5 wt %), where the average n is 0.7; BAYHYDUR N304 and BAYHYDUR N305, which are aliphatic water-dispersible polyisocyanates based on hexamethylene diisocyanate; DESMODUR N3600, DESMODUR N3700, and DESMODUR N3900, which are low viscosity, polyfunctional aliphatic polyisocyanates based on hexamethylene diisocyanate; DESMODUR 3600 and DESMODUR N100 which are aliphatic polyisocyanates based on hexamethylene diisocyanate, commercially available from Bayer Corporation, Pittsburgh, Pa.; PAPI 27 (PMDI commercially available from Dow Chemical having an average molecular weight of 340 and containing NCO 31.4 wt %) where the average n is 0.7; MONDUR MR (PMDI containing NCO at 31 wt % or greater, commercially available from Bayer) where the average n is 0.8; MONDUR MR Light (PMDI containing NCO 31.8 wt %, commercially available from Bayer) where the average n is 0.8; MONDUR 489 (PMDI commercially available from Bayer containing NCO 30-31.4 wt %) where the average n is 1.0; poly[(phenylisocyanate)-co-formaldehyde] (Aldrich Chemical, Milwaukee, Wis.), other isocyanate monomers such as DESMODUR N3200 (poly(hexamethylene diisocyanate) commercially available from Bayer), and TAKENATE D110-N(xylene diisocyanate adduct polymer commercially available from Mitsui Chemicals corporation, Rye Brook, N.Y., containing NCO 11.5 wt %), DESMODUR L75 (a polyisocyanate base on toluene diisocyanate commercially available from Bayer), and DESMODUR IL (another polyisocyanate based on toluene diisocyanate commercially available from Bayer).

In some embodiments, the polyisocyanate used in the preparation of the capsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea/polyureathane polymers as capsule wall materials.

The average molecular weight of certain suitable polyisocyanates varies from 250 to 1000 Da and preferable from 275 to 500 Da. In general, the range of the polyisocyanate concentration varies from 0.1% to 10%, preferably from 0.1% to 8%, more preferably from 0.2 to 5%, and even more preferably from 1.5% to 3.5%, all based on the weight of the capsule delivery system.

1.1.2 Carbonyl Crosslinker

The carbonyl crosslinkers each have at least two functional groups, e.g., a first functional group and a second functional group.

The first functional group is an electrophilic group reactive towards the polyfunctional amine or the polyfunctional alcohol to form a network of the encapsulating polymer. Examples include formyl, keto, carboxyl, a carboxylate ester group, an acyl halide group, an amide group, a carboxylic anhydride group, an alkyl halide group, an epoxide group, an aziridine group, an oxetane group, an azetidine group, a sulfonyl halide group, a chlorophosphate group, an isocyanate group, an α,β-unsaturated carbonyl group, an α,β-unsaturated nitrile group, or an α,β-unsaturated methanesulfonyl group. Preferably, the first function group is a carbonyl electrophilic group containing a carbonyl group such as formyl, keto, carboxyl, a carboxylate ester group, an acyl halide group, an amide group, a carboxylic anhydride group, an α,β-unsaturated carbonyl group, a trifluoromethanesulfonate group, and a p-toluenesulfonate group.

The second functional group is an electrophilic group reactive towards the polyfunctional amine or the polyfunctional alcohol. It can be selected from the groups listed immediately above.

Examples of a carbonyl crosslinker include glutaric dialdehyde, succinic dialdehyde, and glyoxal; as well as compounds such as glyoxyl trimer and paraformaldehyde, bis (dimethyl) acetal, bis(diethyl) acetal, polymeric dialdehydes, such as oxidized starch. Preferably the crosslinking agent is a low molecular weight, difunctional aldehyde, such as glyoxal, 1,3-propane dialdehyde, 1,4-butane dialdehyde, 1,5-pentane dialdehyde, or 1,6-hexane.

1.1.3 Polyfunctional Amines

Suitable polyfunctional amines include those described in WO 2015/023961. Examples are hexamethylenediamine, hexaethylenediamine, ethylenediamine, 1,3-diaminopropane, 1,4-diamino-butane, diethylenetriamine, pentaethylenehexamine, bis(3-aminopropyl)amine, bis(hexamethylene) triamine, tris(2-aminoethyl)amine, triethylene-tetramine, N,N'-bis(3-aminopropyl)-1,3-propanediamine, tetraethylenepentamine, amino-2-methyl-1-propanol, chitosan, 1,3- diamino-guanidine, 1,1-dimethylbiguanide, guanidine, arginine, lysine, histidine, ornithine, nisin, gelatin, and combinations thereof.

Other suitable polyamines include polyethylenimine and branched polyethylenimine ("BPEI"). Representative BPEI structure is shown below:

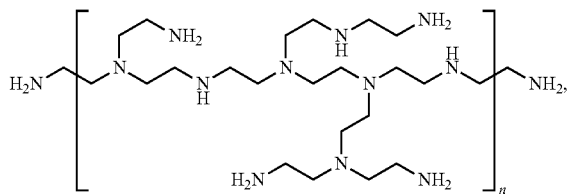

in which n is an integer from 1 to 20,000 (e.g., 1 to 10,000, 2 to 5,000, and 2 to 1,000). BPEI for use in this invention preferably has a molecular weight of 500 to 5,000,000 Daltons (e.g., 500 to 1,000,000 Daltons, 750 to 500,000 Daltons, 750 to 100,000 Daltons, and 750 to 50,000 Daltons).

BPEI are commercially available from Sigma-Aldrich (St. Louis, Mo.; average molecular weight 25,000 Daltons) and Polysciences Inc. (Warrington, Pa.; various products having molecular weight of 600, 1200, 1800, 10,000, 70,000, 750, 000, 250,000, and 2,000,000 Daltons).

1.1.4 Polyfunctional Alcohols

Suitable polyfunctional alcohols are also described in WO 2015/023961. Examples include pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, and combinations thereof.

1.2 Aminoplast and Gelatin Microcapsules

A representative process used for aminoplast encapsulation is disclosed in US 2007/0078071, though it is recognized that many variations with regard to materials and process steps are possible. Another encapsulation process, i.e., gelatin encapsulation, is disclosed in U.S. Pat. No. 2,800,457. Both processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in Application GB 2006709 A; the production of micro-capsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules (see EP 0 158 449 A1); etherified urea-formaldehyde polymers (see U.S. Pat. No. 5,204,185); melamine-formaldehyde microcapsules as described in U.S. Pat. No. 4,525,520; cross-linked oil-soluble melamine-formaldehyde precondensates as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymers as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine-formaldehyde pre-condensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alcohol, e.g., methanol, ethanol, 2-propanol, 3-propanol, 1-butanol, 1-pentanol or 1-hexanol, thereby forming a partial ether where the mole ratio of melamine/urea:formaldehyde:alcohol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. Nos. 3,516,846 and 6,261,483, and Lee et al. (2002) J. Microencapsulation 19, 559-569.

Examples of urea-formaldehyde pre-condensates useful in the practice of this invention are URAC 180 and URAC 186, trademarks of Cytec Technology Corp. of Wilmington, Del. Examples of melamine-formaldehyde pre-condensates useful in the practice if this invention, include, but are not limited to, CYMEL U-60, CYMEL U-64 and CYMEL U-65, trademarks of Cytec Technology Corp. of Wilmington, Del. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from about 9:1 to about 1:9, preferably from about 5:1 to about 1:5 and most preferably from about 2:1 to about 1:2.

In one embodiment, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN series of polyvinyl formamides available from BASF. The molecular weights of these materials can range from 10,000 to 1,000,000 Daltons.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

1.3 Sol-Gel Microcapsules

Sol-gel microcapsules each have a sol-gel polymer as the encapsulating polymer. The sol-gel polymer is the polymerization product of a sol-gel precursor, a compound capable of forming a sol-gel polymer. The sol-gel precursors are typically those containing silicon, boron, aluminum, titanium, zinc, zirconium, and vanadium. Preferred precursors are organosilicon, organoboron, organoaluminum including metal alkoxides and b-diketonates, and combinations thereof. See U.S. Pat. No. 9,532,933.

1.4 Hydrogel Microcapsules

Hydrogel microcapsules are prepared using a polymerizable material such as a monofunctional or multifunctional acrylic or methacrylic acid, or ester thereof. See e.g., WO2014/011860. Exemplary materials useful for preparing hydrogel microcapsules are listed below.

1.4.1 Monomers

Preferred bi- or polyfunctional vinyl monomers include by way of illustration and not limitation, acrylic acid, methacrylic acid, 2-hydroxyethyl acrylate, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-ethylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylhexyl acrylate, 2-ethylhexyl acrylate, 1-methylheptyl acrylate, 4-ethyl-1-methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate, triethylene glycol diacrylate, triethylene glycol dimethacrylate, diethylene glycol diacrylate, diethylene glycol dimethacrylate, tripropylene glycol diacrylate, aliphatic or aromatic urethane diacrylates, difunctional urethane acrylates, ethoxylated bisphenol diacrylate, ethoxylated bisphenol dimethylacrylate, ethoxylated aliphatic difunctional urethane methacrylates, ethoxylated trimethylolpropane triacrylate, ethoxylated pentaerythritol tetraacrylate, dipropylene glycol diacrylate, aliphatic or aromatic urethane dimethacrylates, epoxy acrylates, epoxymethacrylates, tetraethylene glycol dimethacrylate, tetraethylene glycol diacrylate, polyethylene glycol dimethacrylate, polyethylene glycol diacrylate, 1,3-butylene glycol diacrylate, 1,3-butylene glycol dimethacrylate, 1,4-butanediol dimethacrylate, 1,4-butaneidiol diacrylate, 1,6-hexanediol diacrylate, 1,6-hexanediol dimethacrylate, neopentyl glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpropane triacrylate, pentaerythritol triacrylate, propoxylated trimethylolpropane triacrylate, propoxylated glyceryl triacrylate, ditrimethyloipropane tetraacrylate, dipentaerythritol pentaacrylate, and the like. Representative ester monomers of methacrylic acid, which can be used include 2-hydrox ethyl methacrylate, glycidyl methacrylate, methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, 2-(dimethylamino)ethyl methacrylate, 2-(diethylamino)ethyl methacrylate, 2-(diisopropylamino)ethyl methacrylate, N-(2-aminoethyl)methacrylamide hydrochloride, 2-aminoethyl methacrylate hydrochloride, N-(3-aminopropyl)methacrylamide hydrochloride, 2-(tert-butylamino)ethyl methacrylate, and the like.

The above monomers may be employed separately or in various mixtures. The use of multifunctional acrylate and methacrylate will lead to the formation of cross-linked network polymers upon polymerization. Such polymers have desirable properties such as good mechanical strength, elasticity, toughness, and flexibility. Examples of multifunctional acrylates and methacrylates of use in this invention include, but are not limited to, ethylene glycol dimethacrylate (EGDMA), trimethylolpropane trimethacrylate, trimethyloyl triacrylate, pentaerythritol triacrylate, pentaerythritol tetracrylate, bisphenol A dimethacrylate, di (trimethylolpropane) tetraacrylate (DTTA), 1-(acryloyloxy)-3-(methacryloyloxy)-2-propanol (AOOP), trimethylolpropane ethoxylate triacrylate (TPETA), dipentaerythritol pentaacrylate, hexane diacrylate, poly (ethylene glycol) dimethacrylate (PEGDMA), and 1,6-hexanediol dimethacrylate (HDDMA), 1,4-butandiol dimethacrylate, 1,3-butandiol dimethacrylate, 1,6-hexanediol diacrylate, 1,4-butandiol diacrylate, 1,3-butandiol diacrylate.

In certain embodiments, the acrylic or methacrylic acid, or ester thereof, makes up less than 25% by mass, preferably 5 to 20% by mass, or more preferably 10 to 15% by mass of the oil phase.

1.4.2 Initiators

Initiators are often used to start the polymerization reactions. Examples include but not limited to: AIBN, sodium persulfate, benzoyl peroxide, and ammonium persulfate.

1.5 Coacervate Capsules

Proteins useful in coacervation processes include albumins, vegetable globulins and gelatines. The gelatine may be fish, pork, beef, and/or poultry gelatine, for example. According to a preferred embodiment, the protein is fish, beef or poultry gelatine. According to a more preferred embodiment, the protein is warm water fish gelatine.

Typical non-protein polymers useful in complex coacervation methods include, in particular, negatively charged polymers. For example, they may be selected from gum arabic, xanthan, agar, alginate salts, cellulose derivatives, for example carboxymethyl cellulose, pectinate salts, carrageenan, polyacrylic and methacrylic acid, and/or mixtures thereof. Further suitable non-proteins can be derived from the literature, for example from to WO 2004/022221.

A cross-linking agent is typically used to harden the coating layer. Suitable cross-linking agents include formaldehyde, acetaldehyde, glutaraldehyde, glyoxal, chrome alum, or transglutaminase. Preferably, transglutaminase is used at 10-100, preferably 30-60 activity units per gram of gelatine. This enzyme is well described and commercially obtainable.

1.6 Microcapsule Formation Aids

Most microcapsule formation aids are used as dispersants (namely, emulsifiers or surfactants). They facilitate the formation of stable emulsions containing nano- or micro-sized oil drops to be encapsulated. Further, microcapsule formation aids improve the performance of the microcapsule by stabilizing capsules and/or their deposition to the target areas or releasing to the environment. Performance is measured by the intensity of the fragrance release during the use experience, such as the pre-rub and post-rub phases in a laundry experience. The pre-rub phase is the phase when the microcapsules have been deposited on the cloth, e.g., after a fabric softener containing microcapsules has been used during the wash cycle. The post-rub phase is after the microcapsules have been deposited and the microcapsules are broken by friction or other similar mechanisms.

The amount of these microcapsule formation aids is anywhere from about 0.1 to about 40 percent by weight of the microcapsule, more preferably from 0.1 to about 10 percent, more preferably 0.1 to 5 percent by weight.

Preferred microcapsule formation aids are polyvinyl pyrrolidone, polyvinyl alcohol, poly(styrene sulfonate), carboxymethyl cellulose, sodium salt of naphthalene sulfonate condensate, co-polymer of ethylene and maleic anhydride, an alginate, hyaluronic acid, poly(acrylic acid), carboxymethylcellulose, copolymers of acrylic acid and acrylamide, copolymer of acrylamide and acrylamidopropyltrimonium chloride, terpolymers of (acrylic acid, acrylamide, and acrylamidopropyltrimonium chloride), partially or completely hydrolyzed polyvinyl acetate polymers (i.e., polyvinyl alcohol), and combinations thereof.

Other microcapsule formation aids include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, cellulose sulfate and pectin, isobutylene-maleic anhydride copolymer, gum arabic, carrageenan, sodium alginate, pectic acid, tragacanth gum, almond gum and agar; semi-synthetic polymers such as sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Commercially available surfactants include, but are not limited to, sulfonated naphthalene-formaldehyde condensates such as MORWET D425 (sodium salt of alkylnaphthalenesulfonate formaldehyde condensate, Akzo Nobel, Fort Worth, Tex.); partially hydrolyzed polyvinyl alcohols such as MOWIOLs, e.g., MOWIOL 3-83 (Air Products), Ultalux FP, Ultalux FA, Ultalux AD, Selvol 203 (Sekisui), OKS-8089 (Sourus); ethylene oxide-propylene oxide block copolymers or poloxamers such as PLURONIC, SYNPERONIC or PLURACARE materials (BASF); sulfonated polystyrenes such as FLEXAN II (Akzo Nobel); ethylene-maleic anhydride polymers such as ZEMAC (Vertellus Specialties Inc.); copolymer of acrylamide and acrylamidopropyltrimonium chloride such as Salcare SC 60 (BASF); and Polyquaternium series such as Polyquaternium 11 ("PQ11;" a copolymer of vinyl pyrrolidone and quaternized dimethylaminoethyl methacrylate; sold by BASF as LUVIQUAT PQ11 AT 1). Surfactant MOWIOL 3-83 has a viscosity of 2-4 mPa·S (e.g., 3 mPa·S), a degree of hydrolysis of 80-85% (e.g., 83%), an ester value of 170-210 mg KOH/g (e.g., 190 mg KOH/g), and a residual unhydrolyzed acetyl content of 13-18% (e.g., 15%).

In other embodiments, the capsule formation aid is a processing aid such as hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), Ultrez 20 (Acrylates/C10-30 Alkyl Acrylate Crosspolymer), Carbopol® Ultrez 30 (crosslinked homopolymer of acrylic acid polymerized in a cyclohexane and ethyl acetate co-solvent system), Aculyn Excel (Acrylates Copolymer), Carbopol 981 (Carbomer), and the like, and their quaternized forms.

The capsule formation aid may also be used in combination with carboxymethyl cellulose ("CMC"), polyvinylpyrrolidone, polyvinyl alcohol, alkylnaphthalenesulfonate formaldehyde condensates, and/or a surfactant during processing to facilitate capsule formation. Examples of surfactants that can be used in combination with the capsule formation aid include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. In certain embodiments, the CMC polymer has a molecular weight range between about 90,000 Daltons to 1,500,000 Daltons, preferably between about 250,000 Daltons to 750,000 Daltons and more preferably between 400,000 Daltons to 750,000 Daltons. The CMC polymer has a degree of substitution between about 0.1 to about 3, preferably between about 0.65 to about 1.4, and more preferably between about 0.8 to about 1.0. The CMC polymer is present in the capsule slurry at a level from about 0.1% to about 2% and preferably from about 0.3% to about 0.7%. in other embodiments, polyvinylpyrrolidone used in this invention is a water-soluble polymer and has a molecular weight of 1,000 to 10,000,000. Suitable polyvinylpyrrolidone are polyvinylpyrrolidone K12, K15, K17, K25, K30, K60, K90, or a mixture thereof. The amount of polyvinylpyrrolidone is 2-50%, 5-30%, or 10-25% by weight of the capsule delivery system. Commercially available alkylnaphthalenesulfonate formaldehyde condensates include MORWET D-425, which is a sodium salt of naphthalene sulfonate condensate by Akzo Nobel, Fort Worth, Tex.

In food products, food-grade dispersants are use. The term "food-grade dispersant" refers to a dispersant having a quality as fit for human consumption in food. They can be natural or non-natural products. A natural product or surfactant refers to a product that is naturally occurring and comes from a nature source. Natural products/surfactants include their derivatives which can be salted, desalted, deoiled, fractionated, or modified using a natural enzyme or microorganism. On the other hand, a non-natural surfactant is a chemically synthesized surfactant by a chemical process that does not involve an enzymatic modification.

Natural dispersants include quillaja saponin, lecithins, gum arabic, pectin, carrageenan, chitosan, chondroitin sulfate, cellulose gum, modified starch, whey protein, pea protein, egg white protein, silk protein, gelatin of fish, proteins of porcine or bovine origin, ester gum, fatty acids, and combinations thereof.

Non-natural dispersants include N-lauroyl-L-arginine ethyl ester, sorbitan esters, polyethoxylated sorbitan esters, polyglyceryl esters, fatty acid esters, and combination thereof.

Other food safe dispersant can also be included in the microcapsule of this invention. Examples include ammonium phosphatides, acetic acid esters of mono- and diglycerides (Acetem), lactic acid esters of mono- and diglycerides of fatty acids (Lactem), citric acid esters of mono and diglycerides of fatty acids (Citrem), mono and diacetyl tartaric acid esters of mono and diglycerides of fatty acids (Datem), succinic acid esters of monoglycerides of fatty acids (SMG), ethoxylated monoglycerides, sucrose esters of fatty acids, sucroglycerides, polyglycerol polyricinoleate, propane-1,2-diol esters of fatty acids, thermally oxidized soya bean oil interacted with mono- or diglycerides of fatty acids, sodium stearoyl lactylate (SSL), calcium stearoyl lactylate (CSL), stearyl tartrate, polyglycerol esters of interesterified castor oil acid (E476), sodium stearoyllatylate, sodium lauryl sulfate, polyoxyethylated hydrogenated castor oil (for instance, such sold under the trade name CREMOPHOR), block copolymers of ethylene oxide and propylene oxide (for instance as sold under the trade name PLURONIC or the trade name POLOXAMER), polyoxyethylene fatty alcohol ethers, and polyoxyethylene stearic acid ester.

1.7 Additional Wall Polymer

The Encapsulating polymer can also include one or more additional wall polymers, e.g., a second, third, fourth, fifth, or sixth polymer. The additional polymers can be selected from the group consisting of silica, polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof.

1.8 Encapsulation Methods

Conventional encapsulation methods can be used to prepare the reloadable microcapsules. See WO 2015/023961.

By way of illustration, to prepare a reloadable microcapsule having a polyurea encapsulating polymer, an oil-in-water emulsion is first prepared containing (i) a polyamine, a polyalcohol, or mixture thereof, (ii) a polyisocyanate, carbonyl crosslinker, or mixture thereof, (iii) an oil phase having a hydrophilic core solvent and a hydrophobic core solvent, and (iv) an aqueous phase having a microcapsule formation aid and water. The reaction between the polyamine/polyalcohol and the polyisocyanate/carbonyl crosslinker occurs when the temperature of the reaction mixture is raised or a catalyst (such as a transglutaminase for catalyzing amide formation) is added to the mixture.

Catalysts suitable for use in the polyurea/polyurethane formation are transglutaminases, metal carbonates, metal hydroxide, amino or organometallic compounds and include, for example, sodium carbonate, cesium carbonate, potassium carbonate, lithium hydroxide, 1,4-diazabicyclo [2.2.2]octane (i.e., DABCO), N,N-dimethylaminoethanol, N,N-dimethylcyclohexylamine, bis-(2-dimethylaminoethyl) ether, N,N dimethylacetylamine, stannous octoate and dibutyltin dilaurate.

The resultant microcapsule slurry is then cured at a predetermined temperature for a predetermined period of time.

In accordance with some embodiments, the microcapsules prepared according to the methods above are cured at a temperature in the range of, e.g., 15° C. to 230° C. (e.g., 55° C. to 90° C., 55° C. to 75° C., and 90° C. to 130° C.) for 1 minute to 10 hours (e.g., 0.1 hours to 5 hours, 0.2 hours to 4 hours and 0.5 hours to 3 hours). A skilled person in the art can determine, without undue experiments, the curing temperature, duration, and the heating rate.

To obtain microcapsules with more leaching of the active material, certain embodiments of this invention provide for a cure at a low temperature, e.g., less than 100° C. In some embodiments, the cure temperature is at or less than 90° C. In other embodiments, the cure temperature is at or less than 80° C.

In one embodiment, the capsules are heated to a target cure temperature at a linear rate of 0.5 to 2° C. per minute (e.g., 1 to 5° C. per minute, 2 to 8° C. per minute, and 2 to 10° C. per minute) over a period of 1 to 60 minutes (e.g., 1 to 30 minutes). The following heating methods may be used: conduction for example via oil, steam radiation via infrared, and microwave, convection via heated air, steam injection and other methods known by those skilled in the art. The target cure temperature used herein refers to the minimum temperature in degrees Celsius at which the capsules may be cured to retard leaching.

2. Active Materials

The microcapsule compositions of the invention have one or more actives materials in the external hydrophilic solvent. Nonlimiting examples include those described in WO 2016/049456. These active material include flavor or fragrance ingredients, taste masking agents, taste sensates, malodor counteracting agents, vitamins, antibacterials, sunscreen actives, antioxidants, anti-inflammatory agents, anesthetics, analgesics, antifungal agents, antibiotics, anti-viral agents, anti-parasitic agents, anti-infectious and anti-acne agents, dermatological active ingredients, enzymes and co-enzymes, skin whitening agents, anti-histamines, chemotherapeutic agents, and insect repellents. In addition to the active materials listed above, the products of this invention can also contain dyes, colorants or pigments, naturally obtained extracts (for example paprika extract and black carrot extract), and aluminum lakes. The microcapsule compositions of the invention are particularly suitable for encapsulating fragrances containing one or more aldehydes, amines, and/or alcohols. Aldehydes/amines/alcohols can react with microcapsule wall forming materials such as polyisocyanates, silicate, acrylates, etc.

In some embodiments, the amount of active material in the microcapsule composition is from 0.1 to 95% (e.g., 0.5 to 10%, 1 to 90%, 2% to 80%, 4 to 70%, and 5 to 50%) by weight of the composition. The amount of the capsule wall is from 1 to 98% (e.g., 1 to 50%, 2 to 20%, and 3 to 15%)

by weight of the capsule. The amount of the microcapsule core (the sum of the hydrophilic and hydrophobic core solvents) is from 10 to 99% (e.g., 20 to 95%, 50 to 95%, and 80 to 95%) by weight of the capsule.

In some microcapsule compositions, the ratio between the capsule and active material is 1:2 to 40:1 (e.g., 1:1 to 30:1 and 1:1 to 20:1).

3. Adjunct Materials

In addition to the active materials, the present invention also contemplates the incorporation of adjunct materials including solvent, emollients, and core modifier materials in the core encapsulated by the capsule wall. Other adjunct materials are nanoscale solid particulate materials, polymeric core modifiers, solubility modifiers, density modifiers, stabilizers, humectants, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of from 0.01% to 25% (e.g., from 0.5% to 10%) by weight of the capsule.

Suitable examples include those described in WO 2016/049456 and US 2016/0158121.

4. Deposition Aids

A capsule deposition aid from 0.01 to 25%, more preferably from 5 to 20% can be included by weight of the capsule. The capsule deposition aid can be added during the preparation of the capsules or it can be added after the capsules have been made.

These deposition aids are used to aid in deposition of capsules to surfaces such as fabric, hair or skin. These include anionically, cationically, nonionically, or amphoteric water-soluble polymers. Suitable deposition aids include polyquaternium-4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, an acrylamidopropyltrimonium chloride/acrylamide copolymer, a methacrylamidopropyltrimonium chloride/acrylamide copolymer, and combinations thereof. Other suitable deposition aids include those described in WO 2016049456, pages 13-27. Additional deposition aids are described in US 2013/0330292, US 2013/0337023, and US 2014/0017278.

5. Microcapsule Delivery System Formulations

The reloadable microcapsule can be formulated into a capsule delivery system (e.g., a microcapsule composition) for use in consumer products.

The capsule delivery system can be a slurry containing in an external hydrophilic solvent (e.g., water, ethanol, and a combination thereof) the capsule at a level 0.1 to 80% (e.g., 70-75%, 40-55%, 50-90%, 1 to 65%, and 5 to 45%) by weight of the capsule delivery system.

In some embodiments, the capsule and its slurry prepared in accordance with the present invention is subsequently purified. See US 2014/0017287. Purification can be achieved by washing the capsule slurry with water until a neutral pH is achieved.

6. Additional Components

The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. The capsule delivery system can also contain one or more (e.g., two, three, four, five or six more) different capsules including different capsules of this invention and other capsules such as such as aminoplasts, hydrogel, sol-gel, polyurea/polyurethane capsules, and melamine formaldehyde capsules. More exemplary delivery systems that can be incorporated are coacervate capsules (see WO 2004/022221) and cyclodextrin delivery systems (see WO 2013/109798 and US 2011/03085560).

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R or S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Omithine include L-omithine and its salts/hydrates (e.g., monohydrochloride) and D-omithine and its salts/hydrates (e.g., monohydrochloride).

7. Applications

The delivery systems of the present invention are well-suited for use, without limitation, in the following products:

a) Household products
  i. Liquid or Powder Laundry Detergents which can use the present invention include those systems described in U.S. Pat. Nos. 5,929,022, 5,916,862, 5,731,278, 5,565,145, 5,470,507, 5,466,802, 5,460, 752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818 ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).

iii. Scent Boosters such as those described in U.S. Pat. Nos. 7,867,968, 7,871,976, 8,333,289, US 2007/0269651 A1, and US2014/0107010 A1.

iv. Fabric Care Products such as Rinse Conditioners (containing 1 to 30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134

Liquid fabric softeners/fresheners contains at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.

v. Liquid dish detergents such as those described in U.S. Pat. Nos. 6,069,122 and 5,990,065 vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562 vii. All-purpose Cleaners including bucket dilutable cleaners and toilet cleaners viii. Bathroom Cleaners ix. Bath Tissue x. Rug Deodorizers xi. Candles xii. Room Deodorizers xiii. Floor Cleaners xiv. Disinfectants xv. Window Cleaners xvi. Garbage bags/trash can liners xvii. Air Fresheners including room deodorizer and car deodorizer, scented candles, sprays, scented oil air freshener, Automatic spray air freshener, and neutralizing gel beads xviii. Moisture absorber xix. Household Devices such as paper towels and disposable Wipes xx. Moth balls/traps/cakes b) Baby Care Products
  i. Diaper Rash Cream/Balm
  ii. Baby Powder c) Baby Care Devices
  i. Diapers
  ii. Bibs
  iii. Wipes d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.

i. Tooth Paste. An exemplary formulation as follows:
    1. calcium phosphate 40-55%
    2. carboxymethyl cellulose 0.8-1.2%

3. sodium lauryl sulfate 1.5-2.5%
4. glycerol 20-30%
5. saccharin 0.1-0.3%
6. flavor oil 1.0-2.5%
7. water q.s. to 100%

A typical procedure for preparing the formulation includes the steps of (i) mixing by a blender according to the foregoing formulation to provide a toothpaste, and (ii) adding a composition of this invention and blending the resultant mixture till homogeneous.

ii. Tooth Powder
iii. Oral Rinse
iv. Tooth Whiteners
v. Denture Adhesive e) Health Care Devices
i. Dental Floss
ii. Toothbrushes
iii. Respirators
iv. Scented/flavored condoms f) Feminine Hygiene Products such as Tampons, Feminine Napkins and Wipes, and Pantiliners g) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically, i. Personal Cleansers (bar soaps, body washes, and shower gels)
ii. In-shower conditioner
iii. Sunscreen ant tattoo color protection (sprays, lotions, and sticks)
iv. Insect repellants
v. Hand Sanitizer
vi. Antiinflammatory balms, ointments, and sprays
vii. Antibacterial ointments and creams
viii. Sensates
ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant.
x. Wax-based Deodorant. An exemplary formulation as follows:
1. Parafin Wax 10-20%
2. Hydrocarbon Wax 5-10%
3. White Petrolatum 10-15%
4. Acetylated Lanolin Alcohol 2-4%
5. Diisopropyl Adipate 4-8%
6. Mineral Oil 40-60%
7. Preservative (as needed)

The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.

xi. Glycol/Soap Type Deodorant. An exemplary formulation as follows:
1. Propylene Glycol 60-70%
2. Sodium Stearate 5-10%
3. Distilled Water 20-30%
4. 2,4,4-Trichloro-2'-Hydroxy Diphenyl Ether, manufactured by the Ciba-Geigy Chemical Company and a Trademark of the Ciba-Geigy Chemical Company) 0.01-0.5%

The ingredients are combined and heated to 75° C. with stirring until the sodium stearate has dissolved. The resulting mixture is cooled to 40° C. followed by addition of a composition of this invention.

xii. Lotion including body lotion, facial lotion, and hand lotion
xiii. Body powder and foot powder
xiv. Toiletries
xv. Body Spray, aerosol or non-aerosol body spray (WO2014/014705 and WO2016205023)
xvi. Shave cream and male grooming products
xvii. Bath Soak
xviii. Exfoliating Scrub h) Personal Care Devices
i. Facial Tissues
ii. Cleansing wipes i) Hair Care Products
i. Shampoos (liquid and dry powder)
ii. Hair Conditioners (Rinse-out conditioners, leave-in conditioners, and cleansing conditioners)
iii. Hair Rinses
iv. Hair Refreshers
v. Hair perfumes
vi. Hair straightening products
vii. Hair styling products, Hair Fixative and styling aids
viii. Hair combing creams
ix. Hair wax
x. Hair foam, hair gel, nonaerosol pump spray
xi. Hair Bleaches, Dyes and Colorants
xii. Perming agents
xiii. Hair wipes j) Beauty Care
i. Fine Fragrance—Alcoholic. Compositions and methods for incorporating fragrance capsules into alcoholic fine fragrances are described in U.S. Pat. No. 4,428,869. Alcoholic fine fragrances may contain the following:
1. Ethanol (1-99%)
2. Water (0-99%)
3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.1-1%)
4. Optionally an emulsifier or an emollient may be included including but not limited to those listed above ii. Solid Perfume
iii. Lipstick/lip balm
iv. Make-up cleanser
v. Skin care cosmetic such as foundation, pack, sunscreen, skin lotion, milky lotion, skin cream, emollients, skin whitening

- vi. Make-up cosmetic including manicure, mascara, eyeliner, eye shadow, liquid foundation, powder foundation, lipstick and cheek rouge
- k) Consumer goods packaging such as fragranced cartons, fragranced plastic bottles/boxes
- l) Pet care products
  - i. Cat litter
  - ii. Flea and tick treatment products
  - iii. Pet grooming products
  - iv. Pet shampoos
  - v. Pet toys, treats, and chewables
  - vi. Pet training pads
  - vii. Pet carriers and crates
- m) Confectionaries confectionery, preferably selected from the group consisting of chocolate, chocolate bar products, other products in bar form, fruit gums, hard and soft caramels and chewing gum
  - i. Gum
    1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or U.S. Pat. No. 6,986,709) 20-25%
    2. Powdered sugar 45-50%
    3. glucose 15-17%
    4. starch syrup 10-13%
    5. plasticizer 0.1%
    6. flavor 0.8-1.2%
       The components described above were kneaded by a kneader according to the foregoing formulation to provide a chewing gum. Encapsulated Flavor or sensate is then added and blended till homogeneous.
  - ii. Breath Fresheners
  - iii. Orally Dissolvable Strips
  - iv. Chewable Candy
  - v. Hard Candy
- n) Baked products, preferably selected from the group consisting of bread, dry biscuits, cakes and other cookies;
- o) snack foods, preferably selected from the group consisting of baked or fried potato chips or potato dough products, bread dough products and corn or peanut-based extrudates;
  - i. Potato, tortilla, vegetable or multigrain chips
  - ii. Popcorn
  - iii. Pretzels
  - iv. Extruded stacks
- p) Cereal Products preferably selected from the group consisting of breakfast cereals, muesli bars and pre-cooked finished rice products
- q) Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
  - i. Ready to drink liquid drinks
  - ii. Liquid Drink Concentrates
  - iii. Powder Drinks
  - iv. Coffee: Instant Cappuccino
    1. Sugar 30-40%
    2. Milk Powder 24-35%
    3. Soluble Coffee 20-25%
    4. Lactose 1-15%
    5. Food Grade Emulsifier 1-3%
    6. Encapsulated Volatile Flavor 0.01-0.5%
  - v. Tea
  - vi. Alcoholic
- r) Spice blends and consumer prepared foods
  - i. Powder gravy, sauce mixes
  - ii. Condiments
  - iii. Fermented Products
- s) Ready to heat foods: ready meals and soups, preferably selected from the group consisting of powdered soups, instant soups, precooked soups
  - i. Soups
  - ii. Sauces
  - iii. Stews
  - iv. Frozen entrees
- t) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages
  - i. Yoghurt
  - ii. Ice cream
  - iii. Bean Curd
  - iv. Cheese
- u) Soya protein or other soybean fractions, preferably selected from the group consisting of soya milk and products produced therefrom, soya lecithin-containing preparations, fermented products such as tofu or tempeh or products produced therefrom and soy sauces;
- v) Meat products, preferably selected from the group consisting of ham, fresh or raw sausage preparations, and seasoned or marinated fresh or salt meat products
- w) Eggs or egg products, preferably selected from the group consisting of dried egg, egg white and egg yolk
- x) Oil-based products or emulsions thereof, preferably selected from the group consisting of mayonnaise, remoulade, dressings and seasoning preparations
- y) fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables
- z) Flavored pet foods.

The above-listed applications are all well known in the art. For example, fabric softener systems are described in U.S. Pat. No. 6,335,315. Liquid laundry detergents include those systems described in U.S. Pat. No. 5,929,022. Liquid dish detergents are described in U.S. Pat. No. 6,069,122. Shampoo and conditioners that can employ the present invention include those described in U.S. Pat. No. 6,162,423. Automatic Dish Detergents are described in U.S. Pat. No. 6,020,294.

The terms "polyfunctional isocyanate," "multifunctional isocyanate," and "polyisocyanate" all refer to a compound having two or more isocyanate (—NCO) groups.

The terms "polyfunctional amine," "multifunctional amine," and "polyamine" refer to a compound having two or more primary or secondary amine groups. These terms also refer to a compound containing one or more primary/secondary amine groups and one or more hydroxyl groups (—OH).

The terms "microcapsule" and "capsule" are used herein interchangeably.

The terms "polyfunctional alcohol," "multifunctional alcohol," "poly alcohol," and "polyol" refer to a compound having two or more hydroxyl groups.

The invention is described in greater detail by the below non-limiting examples. Without further elaboration, it is believed that one skilled in the art can, based on the description herein, utilize the present invention to its fullest extent. All publications cited herein are incorporated by reference in their entirety.

Example 1: Neobee Oil as the Hydrophobic Core Solvent

A reloadable microcapsule of this invention, i.e., Capsule 1, was prepared following the procedure described below.

More specifically, 120 g of NEOBEE oil (Stepan, Chicago, Ill.; a mixture of caprylic/capric triglycerides) was weighed out and combined with 9.6 g of isocyanate monomer, LUPRANATE M20 (BASF corporation, Wyandotte, Mich.) to form an oil phase. In a separate beaker, a 1% surfactant solution (160 g) was prepared by dissolving 1.6 g of MORWET D-425 (Akzo Nobel, Fort Worth, Tex.) in water. The oil phase was then emulsified into the surfactant solution to form an oil-in-water emulsion under shearing (ULTRA TURRAX, T25 Basic, IKA WERKE) at 9500 rpm for two minutes.

The oil-in-water emulsion was placed in a round bottom vessel and 10.8 g of 40% hexamethylene diamine (HMDA) aqueous solution (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours to obtain Capsule 1. This reloadable microcapsule has (i) a microcapsule wall formed of polyurea and (ii) a microcapsule core consisting of a hydrophobic core solvent (Neobee oil).

The size of the capsule was measure to be in the range of 5-10 microns using a dynamic light scattering (DLS) instrument.

Example 2: Triethyl Citrate as a Hydrophilic Core Solvent

Capsule 2 of this invention was prepared following the same procedure described in Example 1 except that 120 g of triethyl citrate (Vertellus Performance Materials Inc. Greensboro, N.C.) was used instead of Neobee oil.

Capsule 2 has (i) a microcapsule wall formed of polyurea and (ii) a microcapsule core consisting of a hydrophilic core solvent (triethyl citrate).

The size of the capsule was measure to be in the range of 5-10 microns using an DLS instrument.

Example 3: A Mixture of Neobee Oil and Triethyl Citrate in the Core

Capsule 3 of this invention was prepared following the same procedure described in Example 1 except that a mixture of 60 g of triethyl citrate and 60 g of Neobee oil was used instead of Neobee oil.

Capsule 3 has (i) a microcapsule wall formed of polyurea and (ii) a microcapsule core consisting of a hydrophilic core solvent (triethyl citrate) and a hydrophobic core solvent (Neobee oil).

The average particle size of the capsule was measure to be in the range of 5-10 microns using an DLS instrument.

Performance of Reloadable Capsules Blended with Fragrance in Aerosol Base

To establish the consumer benefit of Capsules 1-3, these three reloadable microcapsules in the slurry as prepared each were added, together with fragrance Apple (International Flavors and Fragrance, Union Beach, N.J.), to an aerosol base to obtain three microcapsule compositions, i.e., S1-S3 respectively. Each microcapsule composition contains by weight 4% fragrance, 12.5% capsule slurry and 83.5% aerosol. The composition of the aerosol is provided in Table 1.

A control composition, i.e., Comparative Composition S1', was prepared by mixing 4% fragrance Apple alone with the aerosol base.

TABLE 1

| Ingredient | Description | % |
| --- | --- | --- |
| A46 | Propellant(Butane/Isobutane Mix) | 52.4 |
| Alcohol | Diluent | 42.8 |
| Fragrance | Perfume | 4 |
| Propylene Glycol | Solubilizer | 0.6 |
| COSMOCIL CQ | Deodorant Active | 0.2 |

Each of S1-S3 and S1' (1 g) was sprayed onto a baby T-shirt. Eight T-shirts were evaluated per microcapsule composition by 15 trained judges. The judges rated the fragrance intensity 5 hours after spraying the microcapsule composition and then rubbing (post-rub) the T-shirt for 5 times. The fragrance intensity was rated at a scale ranging from 0 to 10. A numerical value of 2 indicates that the composition produces a weak intensity. A value of 10 indicates that the composition generates a very strong smell.

The sensory results are given in Table 2. The analysis indicated that reloadable capsule compositions (S1-S3) provided significantly greater post-rub fragrance intensity as compared to neat fragrance in Comparative Composition S1').

TABLE 2

| Samples | Post-rubbing fragrance intensity |
| --- | --- |
| S1' (Neat) | 1.93 |
| S1 | 3.79 |
| S2 | 3.14 |
| S3 | 5.07 |

Example 4: A Large Reloadable Capsules with a Mixture of Neobee Oil and Triethyl Citrate (Particle Size: 30 Microns)

A fourth reloadable microcapsule, i.e., Capsule 4, was prepared following the procedure below. NEOBEE oil (120 g) and triethyl citrate (120 g) were combined with 4.8 g of isocyanate monomer, LUPRANATE M20 to form an oil phase. In a separate beaker, a 0.5% surfactant solution (319.2 g) was prepared by dissolving 1.6 g of Mowiol 3-85, a partially hydrolyzed polyvinyl alcohol (Kuraray, Houston, Tex.) in water. The oil phase was then emulsified into the surfactant solution to form an oil-in-water emulsion under shearing (ULTRA TURRAX, T25 Basic, IKA WERKE) at 3000 rpm for three minutes.

The oil-in-water emulsion was placed in a round bottom vessel and 36 g of 6% HMDA aqueous solution was added under constant mixing with an overhead mixer. Formation of capsule was immediately visible by optical microscopy. The mixer speed was reduced after the addition of HMDA was complete. The capsule slurry was cured at 55° C. for three hours to obtain Capsule 4.

The average particle size of the capsule was measure to be 30 microns using an DLS instrument.

Example 5-8: Large (30 Micron) Reloadable Capsules with Different Core Solvents

Capsules 5-8 of this invention were prepared following the same procedure described in Example 4 except that different core solvents were used.

Capsule 5 was prepared using 60 g of triacetin and 180 g of NEOBEE oil.

Capsule 6 was prepared using 60 g of triacetin and 180 g of isopropyl myristate.

Capsule 7 was prepared using 60 g of triethyl citrate and 180 g of isopropyl myristate.

Capsule 8 was prepared using 60 g of triethyl citrate and 180 g of NEOBEE oil.

Each of Capsules 5-8 had an average particle size of 30 microns measured using an DLS instrument.

The Hansen solubility parameters of the core solvents are shown in Table 3 below.

TABLE 3

Hansen Solubility Parameters

| Solvent | δD | δP | δH | Weighted Hansen solubility parameter | Water Solubility (mg/L) |
|---|---|---|---|---|---|
| Preferred hydrophilic core solvent | — | >4 | >5 | >18 | 1000-100,000 |
| triethyl citrate | 16.9 | 6.4 | 10.2 | 20.8 | 65000 |
| triacetin | 16.4 | 5.7 | 9.6 | 19.8 | 21520 |
| Preferred hydrophobic core solvent | — | <4 | <5 | <18 | <1 |
| Neobee oil | 16.5 | 2.5 | 3.3 | 17 | 0.014 |
| isopropyl myristate | 16 | 2.1 | 2.7 | 16.4 | <0.1 |

In some embodiments, the hydrophilic core solvent has a water solubility in the range of 0.02 to 300 g/L (e.g., 0.1 to 200 g/L and 1 to 100 g/L) and a weighted Hansen solubility parameter of 18 or greater. In other embodiments, the hydrophilic core solvent has a Hansen polarizability (dP) of 4 or greater and a Hansen h-bonding value (dH) of 5 or greater. In still other embodiments, the hydrophobic core solvent has a weighted Hansen solubility parameter of 18 or less, a Hansen polarizability (dP) of 4 or less, and a Hansen h-bonding value (dH) of 5 or less. The core solvents used to prepare Capsules 1-8 fall within the above described ranges.

Example 9-12: Performance of Large Reloadable Capsules in an Alcohol Body Spray Base To establish the consumer benefit of reloadable microcapsules, Capsules 4-7 each were mixed with fragrance Apple and then added to an alcohol body spray base (95 wt % ethanol/5 wt % water) to obtain four microcapsule compositions, i.e., S4-S7 respectively. Each microcapsule composition contained by weight 1.5% fragrance, 4.7% capsule slurry and 93.8% alcohol body spray base.

A control composition, i.e., Comparative Composition S2', was prepared by mixing 1.5% fragrance Apple alone with the alcohol body spray base.

Each of S4-S7 and S2' (0.5 g) was sprayed onto a lycra clothes. The clothes were allowed to dry for 24 hours. A panel of 7 judges evaluated the samples and rated the fragrance intensity both prior to rubbing (pre-rubbing) the clothes and after rubbing it (post-rubbing) for 5 times. The fragrance intensity was rated at a scale ranging from 0 to 10. A numerical value of 2 indicates that the composition produces a weak intensity. A value of 10 indicates that the composition generates a very strong smell.

The sensory results are given in Table 4. The analysis indicated that reloadable capsule compositions (S4-S7) provided significantly greater pre-rubbing and post-rubbing fragrance intensity as compared to neat fragrance in Comparative Composition S2').

TABLE 4

| Samples | Core Solvents Hydrophilic/hydrophobic V/V | Pre-rubbing fragrance intensity | Post-rubbing fragrance intensity |
|---|---|---|---|
| S4 | Triethyl citrate/Neobee oil; 50:50 | 4.50 | 5.57 |
| S5 | Triacetin/Neobee oil; 25:75 | 3.14 | 4.14 |
| S6 | Triacetin/Isopropyl myristate; 25:75 | 3.29 | 4.5 |
| S7 | Triethyl citrate/Isopropyl myristate; 25:75 | 4.14 | 5.07 |
| S2' | No core solvents | 2.14 | 2.86 |

Example 13: Performance of Large Reloadable Capsules in an Aerosol Base

The slurry of Capsule 4 was mixed with fragrance Apple and then added to an aerosol base to obtain microcapsule composition S8. Table 5 below shows the components of S8.

A control composition, i.e., Comparative Composition S3', was prepared by mixing 1.5% fragrance Apple alone with the aerosol base.

Each of S8 and S3' (1 g) was sprayed onto a forearm of a panelist. After 5 hours, the panelist was instructed to briefly rub the forearm and rate the fragrance intensity (post-rubbing) at a scale ranging from 0 to 100. A numerical value of 6 indicates that the composition produces a weak intensity. A value of 17 indicates that the composition generates a very strong smell. A value of 55 designates a very strong smell.

The sensory results are shown in Table 6. The analysis indicated that reloadable capsule composition S8 provided significantly greater post-rubbing fragrance intensity as compared to neat fragrance in Comparative Composition S3').

TABLE 5

| Component | Description | % |
| --- | --- | --- |
| A46 | Propellant(Butane/Isobutane Mix) | 55 |
| Alcohol | Diluent | 38.8 |
| Fragrance | Perfume | 1.5 |
| Capsule | Technology | 4.7 |

TABLE 6

| Samples | Post-rubbing intensity |
| --- | --- |
| S3' | 8.68 |
| S8 | 13.86 |

Example 14: Performance in an Alcohol Body Spray Base

The following evaluation shows the benefit of using reloadable capsules to delivery aldehyde fragrance ingredients. It is known that aldehydes react with microcapsule wall-forming materials such as polyisocyanate and polyamine. Encapsulating aldehydes or alcohols using polyurea chemistry is very challenging. The following example provides an effective method to deliver an aldehyde-containing fragrance using reloadable microcapsules.

The slurry of Capsule 4 was mixed with a research fragrance containing an aldehyde (i.e., Fragrance D), and then blended into an aerosol base to obtain microcapsule composition S9, which contains 1.5% fragrance, 4.7% Capsule 4, and 93.8% alcohol body spray base (95% ethanol/5% water). For comparison, Comparative Composition S4' was prepared using Fragrance D alone at 1.5% in the alcohol body spray base.

Each of S9 and S4' (0.5 g) was sprayed onto a piece of lycra clothes. The piece of clothes was allowed to dry for 24 hours. A panel of 9 judges evaluated the samples and rated the fragrance intensity both prior to rubbing (pre-rubbing) the clothes and after rubbing it (post-rubbing) for 5 times. The fragrance intensity was rated at a scale ranging from 0 to 10. A numerical value of 2 indicates that the composition produces a weak intensity. A value of 10 indicates that the composition generates a very strong smell.

The sensory results are given in Table 7. The analysis indicated that reloadable capsule composition S9 successfully delivered aldehyde-containing fragrance and provided significantly greater pre-rubbing and post-rubbing fragrance intensity as compared to neat fragrance in Comparative Composition S4').

TABLE 7

| Samples | Pre-rubbing intensity | Post-rubbing intensity |
| --- | --- | --- |
| S4' | 3.06 | 4.06 |
| S9 | 3.67 | 5.33 |

Example 15: Diffusion of the Fragrance and Hydrophilic Core Solvent

When mixing reloadable microcapsule Capsule 4 with a fragrance, the hydrophilic core solvent (i.e., triethyl citrate) can diffuse out of the reloadable microcapsule and the fragrance can diffuse into the microcapsule.

To determine the amount of the hydrophilic core solvent and fragrance that diffuse through the microcapsule wall, two microcapsule compositions S10 and S11 were prepared by mixing the following components:

S10:1.5% Model Fragrance A, 4.7% Capsule 4 slurry, and 93.8% an alcohol body spray base (95% ethanol/5% water); and S11:1.5% Model Fragrance B, 4.7% Capsule 4 slurry, and 93.8% an alcohol body spray base (95% ethanol/5% water).

The two microcapsule compositions were allowed to sit at the room temperature for 5 days to reach the equilibrium. For each of S10 and S11, the capsules were filtered out of the base using a 1 micron glass microfiber syringe filter (Whatman). The filtrate was collected and analyzed using a gas chromatograph (GC). The % of diffused fragrance was calculated as (Initial fragrance wt %–wt % fragrance in the filtrate)/initial fragrance wt %×100%. The % of diffused triethyl citrate was calculated as (Initial amount of triethyl citrate–the amount of triethyl citrate in the filtrate)/Initial amount of triethyl citrate×100%. S2' described above was also analyzed as a control (data not shown in Table 8). Table 8 below provides the results for the diffusion experiment.

TABLE 8

| S10 | | S11 | |
| --- | --- | --- | --- |
| % of diffused fragrance | % of diffused triethyl citrate | % of diffused fragrance | % of diffused triethyl citrate |
| 6.7 | 85.3 | 6.7 | 85.3 |

Example 16: Melamine-Formaldehyde Reloadable Microcapsule

A melamine-formaldehyde reloadable microcapsule, i.e., Capsule 9, was prepared following the procedure described in Example 2 of U.S. Pat. No. 7,119,057. See also U.S. Pat. No. 7,196,049.

In brief, a copolymer of acrylamide and acrylic acid was first dispersed in water together with a methylated melamine-formaldehyde resin to obtain a polymer solution. A mixture of Neobee oil/triethyl citrate oil was then added into the solution with high speed shearing to form small droplets. Curing of the polymeric film over the oil droplets as capsule wall affected by increasing the solution pH to polymerize the polymers followed by heating the solution to 50 to 125° C.

Melamine-formaldehyde reloadable microcapsule thus prepared in a slurry contained in the microcapsule core by weight a mixture of 30% triethyl citrate and 70% Neobee oil. The microcapsule core, free of an active material, constituted 32% by weight of the microcapsule slurry. Different triethyl citrate/Neobee oil weight ratio can be use, e.g., at a range of 20/80 to 50/50.

Example 17: Polyurea Reloadable Microcapsule

A polyurea reloadable microcapsule, i.e., Capsule 10, was prepared following the procedure below. See also U.S. Pat. No. 8,299,011 B2, Example 1.

Step 1. Preparation of the oil-in-water emulsion. One hundred twenty grams of a Neobee/triethyl citrate oil mixture was weighed out and combined with 9.6 g of isocyanate monomer, Lupranate™ M20 (BASF corporation, Wyandotte, Mich., USA) to form the oil phase. In a separate beaker, a 3% surfactant solution (160 g) was prepared by dissolving 4.8 g of Mowet D-425 (Akzo Nobel, Fort Worth, Tex., USA) in water. The oil phase was then emulsified into the aqueous phase to form an oil-in-water emulsion under shearing (Ultra Turrax®, T25 Basic, IKA™, WERKE) at 6500 rpm for two minutes.

Step 2. Formation of fragrance capsules. The oil-in-water emulsion was placed in a round bottom vessel and to which 10.8 g of 40% hexamethylene diamine (HMDA) (INVISTA, Wichita, Kans., USA) was added under constant mixing with an overhead mixer. Formation of capsule was immediately visible by optical microscopy. The mixer speed was reduced after the addition of HMDA was complete. The capsule slurry was cured at room temperature for three hours.

Capsule 10 thus prepared had (i) a polyurea microcapsule wall and (ii) a microcapsule core consisting of triethyl citrate as the hydrophilic core solvent and Neobee oil as the hydrophobic core solvent. The weight ratio between triethyl citrate and Neobee oil is 30:70.

Example 18-21: Performance in a Liquid Detergent

To determine the performance of Capsules 9 and 10, four microcapsule compositions (i.e., S12-15) were prepared by mixing each of the two capsules slurry obtained in the examples above with a research fragrance (i.e. Fragrance E) and a liquid detergent base (i.e., unfragranced Liquid Tide, commercially available from the Procter & Gamble Company, Cincinnati, Ohio) as follows:

S12: 0.5% fragrance E, 9.5% Capsule 9 slurry, and 90% Liquid Tide;

S13: 0.5% fragrance E, 9.5% Capsule 9 slurry containing on a solid basis 2% polyquaternium-47 (Merquat™ 2001, Lubrizol Corporation, Wickliffe, Ohio), and 90% Liquid Tide;

S14: 0.5% fragrance E, 9.5% Capsule 10 slurry, and 90% Liquid Tide; and

S15: 0.5% fragrance E, 9.5% Capsule 10 slurry containing on a solid basis 1% polyquaternium-6 (Merquat 100, Lubrizol) and 1.5% polyvinyl amine (Lupamin 9095, BASF), and 90% Liquid Tide.

The above compositions were aged for 4 weeks at 45° C.

A control composition, i.e., Comparative Composition S5', was prepared by mixing 0.5% Fragrance E alone with Liquid Tide.

Each of S12-15 and S5' (1 g) was evaluated by conducting a laundry experiment using a US wash machine. In the wash 40 grams of a sample was dosed. Terry towels were washed and then air-dried for 16 hours before being evaluated by a panel of 12 judges. The fragrance intensity was rated by an LMS scale ranging from 0 to 50. A numerical value of 5 suggests that the fabric only produce a very week intensity while a value of 30 indicates that the subject generates a strong smell, and a value of 50 indicates a very strong smell. The sensory results are shown in Table 9.

The analysis indicated that reloadable capsule compositions S12-15 provided significantly greater post-rubbing fragrance intensity as compared to neat fragrance in Comparative Composition S5'.

TABLE 9

| Sample | Post-rubbing fragrance intensity |
|---|---|
| S5' | 4.1 |
| S12 | 6.9 |
| S13 | 8.4 |
| S14 | 5.0 |
| S15 | 6.4 |

Example 22-25: Performance in a Fabric Softener

To determine the performance of Capsules 9 and 10 in a fabric softener, four microcapsule compositions (i.e., S16-19) were prepared by mixing each of the capsule slurries prepared in the examples above with a research fragrance (i.e. Fragrance F) and a liquid fabric softener base (i.e., unfragranced Downy, commercially available from the Procter & Gamble Company, Cincinnati, Ohio) as follows:

S16: 0.5% fragrance F, 9.5% Capsule 9 slurry, and 90% Downy;

S17: 0.5% fragrance F, 9.5% Capsule 9 slurry containing on a solid basis 2% polyquaternium-47 (Merquat™ 2001 commercially available from Lubrizol Corporation, Wickliffe, Ohio), and 90% Downy;

S18: 0.5% fragrance F, 9.5% Capsule 10 slurry, and 90% Downy; and

S19: 0.5% fragrance F, 9.5% Capsule 10 slurry containing on a solid basis 1% polyquaternium-6 (Merquat 100 from Lubrizol) and 1.5% polyvinyl amine (Lupamin 9095, from BASF), and 90% Downy.

The above compositions were aged for 4 weeks at 45° C.

A control composition, i.e., Comparative Composition S6', was prepared by mixing 0.5% Fragrance F alone with Downy.

Each of S12-15 and S5' (1 g) was evaluated by conducting a laundry experiment with a US washing protocol in a US wash machine. After terry towels were washed with an unfragranced Liquid Tide, 35 grams of each fabric softener (i.e., each of S16-19) was added at the rinse stage. The terry towels were air-dried for 16 hours and then evaluated by a panel of 12 judges. The fragrance intensity was rated by an LMS scale ranging from 0 to 50. A numerical value of 5 suggests that the fabric only produce very week intensity while a value of 30 indicates that the subject generates a strong smell, and a value of 50 indicates a very strong smell. The sensory results are shown in Table 10.

TABLE 10

| Sample | Post-rubbing fragrance intensity |
|---|---|
| S6' | 3.8 |
| S16 | 7.2 |
| S17 | 8.3 |
| S18 | 5.9 |
| S19 | 5.8 |

The analysis indicated that reloadable capsule compositions S16-19 provided significantly greater post-rubbing fragrance intensity as compared to neat fragrance in Comparative Composition S6').

Example 26-27: Polyurea Reloadable Microcapsule—Ethanol Charged

To determine the benefit of ethanol charged capsules, Capsule 4 was mixed with both ethanol and fragrance in the below ratios, creating new capsules slurries (Capsules 11 and 12) and allowed to equilibrate for 2 days before use in both fabric softener and body lotion applications. Ethanol charged Capsule 11 was prepared by mixing 30 g of capsule 4 with 30 g of ethanol and 4.8 g of Fragrance Apple and allowing the mixture to stand for 2 days before use in the application. Capsule 12 was prepared by was prepared by mixing 6.25 g of capsule 4 with 2 g of ethanol and 2.75 g of Fragrance Apple and allowing the mixture to stand for 2 days before use in the application.

Example 28-29: Performance of Ethanol Charged Polyurea Reloadable Microcapsule in Body Lotion To determine the performance of Capsule 11, two microcapsule compositions (i.e., S20-21) were prepared by mixing the Capsule 11 slurry into body lotion base (i.e., unfragranced Lubriderm, commercially available from the Johnson & Johnson Consumer Products Company, Skillman, N.J.) as follows: (i) S20 (uncharged): 2% Fragrance Apple, 12.5% Capsule 4 slurry, and 85.5% Lubriderm body lotion, (ii) S21 (ethanol charged): 12.5% Capsule 4 slurry, 12.5% ethanol, and 73% Lubriderm body lotion. The above compositions were aged for 3 days at room temperature.

A control composition, i.e., Comparative Composition S6', was prepared by mixing 2% Apple Fragrance alone with 98% Lubriderm body lotion.

Each of S20-21 and S6' (0.35 g) were applied to a blotter and evaluated after 24 by a panel of 8 judges for post rub fragrance intensity. The fragrance intensity was rated by a scale ranging from 0 to 10. A numerical value of 2 suggests that the blotter only produce very week intensity while a value of 5 indicates that the subject generates a moderately strong smell, and a value of 8 indicates a very strong smell. The sensory results are shown in Table 11.

TABLE 11

| Sample | Post-rubbing fragrance intensity |
| --- | --- |
| S6' | 4.87 |
| S20 | 6.56 |
| S21 | 7.9 |

The analysis indicated that ethanol charged reloadable capsule compositions S21 provided significantly greater post-rubbing fragrance intensity as compared to neat fragrance (Comparative Composition S6') or the capsule without ethanol charge (Comparative Composition S20').

Example 30-32: Performance of Ethanol Charged Polyurea Reloadable Microcapsule in a Fabric Softener To determine the performance of Capsule 12 in a fabric softener, two microcapsule compositions (i.e., S22-23) were prepared by mixing each of the capsule slurries prepared in the examples above with an Apple fragrance and a liquid fabric softener base (i.e., unfragranced Downy, commercially available from the Procter & Gamble Company, Cincinnati, Ohio) as follows:

S22: 0.423% Fragrance Apple, 1.5% Capsule 4 slurry, and 98.07% Downy; and
S23: 4.1% Capsule 12 slurry, and 95.9% Downy
The above compositions were aged for 4 weeks at 37° C.

A control composition, i.e., Comparative Composition S6', was prepared by mixing 0.423% Fragrance Apple alone with Downy.

Each of S22-23 and S6' (40 g) was evaluated by conducting a laundry experiment with a US washing protocol in a US wash machine. After terry towels were washed with an unfragranced Liquid Tide, 40 grams of each fabric softener (i.e., each of S22-23 and S6') was added at the rinse stage. The terry towels were then placed in a drying cabinet at 75° F. for 4 hours and then evaluated by a panel of 7 judges. The fragrance intensity was rated by a scale ranging from 0 to 10. A numerical value of 2 suggests that the fabric only produce very week intensity while a value of 5 indicates that the subject generates a moderately strong smell, and a value of 8 indicates a very strong smell. The sensory results are shown in Table 12.

TABLE 12

| Sample | Post-rubbing fragrance intensity |
| --- | --- |
| S6' | 1.83 |
| S22 | 3.67 |
| S23 | 4.25 |

The analysis indicated that reloadable capsule compositions S23 provided significantly greater post-rubbing fragrance intensity as compared to neat fragrance (Comparative Composition S6') or the capsule without ethanol charge (Comparative Composition S22').

Example 33: Body Mist

A stable capsule suspension, i.e., S24, was prepared using a visco-stable hydro-alcohol base. Specifically, 0.25 g of Ultrez 20 (a crosspolymer of acrylates/$C_{10}$-$C_{30}$ alkyl acrylate, Lubrizol) was slowly added to 20.75 g of water with mixing, followed by the addition of 70 g of SD alcohol 40 (denatured alcohol) to obtain an Ultra20 hydro-alcohol solution. Subsequently, a slurry of Capsule 4 (5 g) was added and mixed until uniform, to which was then added 4 g of Model Fragrance C. The viscosity of the resultant mixture was adjusted with AMP-Ultra PC 2000 (95% Aminomethyl Propanol (AMP)—Angus Chemical Company) to a viscosity of 350-500 cP. The viscosity was measured using a Brookfield with spindle #4 at a motor speed of 60 RPM. A control composition, i.e., Comparative Composition S24', was prepared similarly except that no capsule slurry was added. Table 13 and 14 below shows the components of S24 and S24' respectively.

Each of S24 and S24' (0.35 g) was sprayed onto a forearm of a panelist. After 5 hours, the panelist was instructed to briefly rub the forearm and rate the fragrance intensity at a scale ranging from 0 to 100. A numerical value of 6 indicates that the composition produces a weak intensity. A value of 17 indicates a strong smell. A value of 55 designates a very strong smell.

S24 had a post-rubbing intensity of 10.4. Comparative Composition S24' had a post-rubbing intensity of 6.9.

TABLE 13

| Component | Description | % |
| --- | --- | --- |
| S24 | | |
| Ultrez 20 | Rheology modifier | 0.25 |
| Water | Base | 20.75 |
| 95% Ethanol | Base | 70 |
| Capsule | Reloadable capsule | 5 |
| Model Fragrance C | Perfume | 4 |

TABLE 14

| Component | Description | % |
| --- | --- | --- |
| S24' | | |
| Ultrez 20 | Rheology modifier | 0.25 |
| Water | Base | 25.75 |
| 95% Ethanol | Base | 70 |
| Model Fragrance C | Perfume | 4 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of preparing a reloadable microcapsule and a composition containing the reloadable microcapsule, one skilled in the art can choose different wall-forming materials/encapsulating polymers, hydrophilic core solvents, hydrophobic core solvents, external hydrophilic solvents, active materials, and/or capsule formation aids/catalysts, varying the concentrations of these wall-forming materials and/or catalysts to achieve desirable thickness of the wall/diffusion rate/organoleptic or release profiles in a consumer product. Further, the ratios among their wall-forming materials, capsule forming aids, adjuvents, core modifiers, active materials, and catalysts can also be determined by a skilled artisan without undue experimentation.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A microcapsule comprising a microcapsule core and a microcapsule wall encapsulating the microcapsule core, said microcapsule charged with ethanol,
wherein
the microcapsule core contains a hydrophobic solvent selected from the group consisting of isopropyl myristate, $C_5$-$C_{50}$ triglyceride, and a combination thereof; and a hydrophilic solvent selected from the group consisting of triethyl citrate, triacetin, dipropylene glycol, and a combination thereof, and
the microcapsule wall, formed of at least one encapsulating polymer, is permeable to the hydrophilic solvent.

2. The microcapsule of claim 1, wherein the microcapsule core is free of an active material; the hydrophilic solvent of the core has a water solubility of 1 g/L to 100 g/L, a weighted Hansen solubility parameter of 18 or greater, a Hansen polarizability of 4 or greater, and a Hansen hydrogen bonding value of 5 or greater; and the hydrophobic core solvent has a weighted Hansen solubility parameter of 18 or less, a Hansen polarizability of 4 or less, and a Hansen h-bonding value of 5 or less.

3. The microcapsule of claim 1, wherein the microcapsule has a size of 0.1 μm to 1000 μm in diameter as determined by dynamic light scattering, the weight ratio between the hydrophobic solvent of the core and the hydrophilic solvent of the core is 1:9 to 9:1, and the weight ratio between the microcapsule core and the microcapsule wall is 50:1 to 1:1.

4. The microcapsule of claim 1, wherein the encapsulating polymer is a polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), or a combination thereof.

5. A microcapsule composition comprising the microcapsule of claim 1 and a continuous phase that has an external hydrophilic solvent and an active material, wherein the microcapsule wall is permeable to the active material, the weight ratio between the microcapsule core and the active material is 1:99 to 99:1, and the active material is selected from the group consisting of a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, taste modulator, cell, probiotic, and combinations thereof.

6. The microcapsule composition of claim 5, wherein the external hydrophilic solvent is water, ethanol, propanol, dipropylene glycol, propylene glycol, glycerin, diethyl phthalate, or a combination thereof.

7. The microcapsule composition of claim 5, wherein the active material is a fragrance having a weighted Hansen solubility parameter of 15 to 20, a Hansen polarizability of 5 or less, and a Hansen hydrogen bonding value of 10 or less.

8. The microcapsule composition of claim 5, wherein the Euclidean difference in weighted Hansen solubility parameter between the fragrance and the hydrophilic solvent of the core is less than the Euclidean difference between the fragrance and the hydrophobic core solvent of the core, wherein the Euclidean difference is calculated as $(4*(\delta D_{solvent}-\delta D_{fragrance})^2+(\delta P_{solvent}-\delta P_{fragrance})^2+(\delta H_{solvent}-\delta H_{fragrance})^2)^{0.5}$, in which $\delta D_{solvent}$, $\delta P_{solvent}$ and $\delta H_{solvent}$ are Hansen dispersion value, Hansen polarizability value and Hansen hydrogen bonding of the solvent, respectively; and $\delta D_{frarance}$, $\delta P_{fragrance}$ and $\delta H_{fragrance}$ are Hansen dispersion value, Hansen polarizability value and Hansen hydrogen bonding of the fragrance, respectively.

9. The microcapsule composition of claim 6, wherein the Euclidean difference in weighted Hansen solubility parameter between the fragrance and the hydrophobic core solvent of the core is less than 5, wherein the Euclidean difference is calculated as $(4*(\delta D_{solvent}-\delta D_{fragrance})^2+(\delta P_{solvent}-\delta P_{fragrance})^2+(\delta H_{solvent}-\delta H_{fragrance})^2)^{0.5}$, in which $\delta D_{solvent}$, $\delta P_{solvent}$ and $\delta H_{solvent}$ are Hansen dispersion value, Hansen polarizability value and Hansen hydrogen bonding of the solvent, respectively; and $\delta D_{fragrance}$, $\delta P_{fragrance}$ and $\delta H_{fragrance}$ are Hansen dispersion value, Hansen polarizability value and Hansen hydrogen bonding of the fragrance, respectively.

10. The microcapsule composition of claim 5, further comprising a deposition aid selected from the group consisting of polyquaternium-4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, and combinations thereof.

\* \* \* \* \*